United States Patent [19]

Ito et al.

[11] Patent Number: 4,920,138
[45] Date of Patent: Apr. 24, 1990

[54] 2(4-CHLOROBENZYL)1(1H-1,2,4-TRIAZOL-1-YL-METHYL-1-CYCLOHEPTANOL AND CYCLOHEXANOL

[75] Inventors: Atsushi Ito; Satoru Kumazawa; Nobuo Sato; Toshihide Saishoji, all of Iwaki, Japan

[73] Assignee: Kureha Kagaku Kogyo Kabushiki Kaishi, Chuo, Japan

[21] Appl. No.: 295,404

[22] Filed: Jan. 10, 1989

[30] Foreign Application Priority Data

Jan. 14, 1988 [JP] Japan .................................. 63-6054

[51] Int. Cl.$^5$ .................. A01N 43/653; C07D 249/12
[52] U.S. Cl. .................... 514/383; 548/341; 548/262.2; 514/385
[58] Field of Search .......................... 514/383; 548/262

[56] References Cited

U.S. PATENT DOCUMENTS

| | | | |
|---|---|---|---|
| 4,499,281 | 2/1985 | Holmwood | 548/262 |
| 4,503,062 | 3/1985 | Gravestock | 548/262 |
| 4,623,654 | 11/1986 | Parry | 548/262 |
| 4,684,396 | 8/1987 | Clough et al. | 548/262 |
| 4,719,307 | 1/1988 | Lantzsch | 548/262 |
| 4,863,505 | 9/1989 | Kumazawa | 548/262 |

FOREIGN PATENT DOCUMENTS 0152031 8/1985 European Pat. Off. .
0272895 6/1988 European Pat. Off. ............ 548/262
2180236 3/1987 United Kingdom ................ 548/262

OTHER PUBLICATIONS

Chem. Abstr., vol. 109, Entry 50257(d) (1968).

Primary Examiner—Donald G. Daus
Attorney, Agent, or Firm—Nixon & Vanderhye

[57] ABSTRACT

Disclosed herein are (1) a novel azole-substituted cycloalkanol derivative represented by the formula (I):

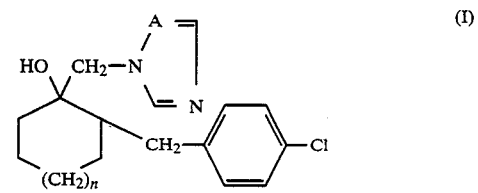

wherein n is an integer of 1 or 2 and A represents a nitrogen atom or a CH group, (2) an agricultural and horticultural fungicide having said cycloalkanol derivative as an active ingredient, (3) a process for producing said cycloalkanol derivative and (4) several novel intermediate compounds to produce said cycloalkanol derivative.

6 Claims, 5 Drawing Sheets

2(4-CHLOROBENZYL)1(1H-1,2,4-TRIAZOL-1-YL-METHYL-1-CYCLOHEPTANOL AND CYCLOHEXANOL

BACKGROUND OF THE INVENTION:

The present invention relates to azole-substituted cycloalkanol derivatives having an activity to control plant diseases, agricultural and horticultural fungicides having the above derivative as an active ingredient and processes to produce the derivatives.

So far, although many compounds have been developed and used as agricultural and horticultural fungicides, they have such defects that their active range to plant diseases is narrow, their toxicity to human and animals is strong, they are not safe in handling and the present situation is that the wholly satisfactory agricultural and horticultural fungicide is scarcely present.

As a result of the present inventors' extensive study to develope an agricultural and horticultural fungicide not having these defects, they have reached to the conclusion that the objective fungicide is probable to be found among cycloalkanol derivatives. Accordingly, they have synthesized many cycloalkanol derivatives and tested their activity and finally they have found that the azole-substituted cycloalkanol derivatives represented by the following formula (I):

wherein n represents an integer of 1 or 2 and A represents a nitrogen atom or a CH group; are low in toxicity to mammals and have an excellent activity to control many plant diseases of a broad range and has been attained the present invention.

SUMMARY OF THE INVENTION:

The object of the present invention is to provide an agricultural and horticultural fungicide which is low in toxicity to mammals and has an excellent activity to control many plant diseases of a broad range.

Further, the object of the present invention is to provide an agricultural and horticultural fungicide containing an azole-substituted cycloalkanol derivative as an active ingredient.

Still further, the object of the present invention is to provide a novel azole-substituted cycloalkanol derivative.

Still more, the object of the present invention is to provide a process to produce the azole-substituted cycloalkanol derivative.

Moreover, the object of the present invention is to provide a useful and novel intermediate in the manufacturing of the azole-substituted cycloalkanol derivative.

DETAILED EXPLANATION OF THE INVENTION:

The present invention has been composed of the novel azole-substituted cycloalkanol derivative represented by the following formula (I):

wherein n represents an integer of 1 or 2 and A represents a nitrogen atom or a CH group; the process for producing the azole-substituted cycloalkanol derivative; the compound groups such as oxirane derivatives, methylenecycloalkane derivatives, cycloalkanone derivatives and cycloalkanecarboxylic acid ester derivatives which can be used as an intermediate in the production of the azole-substituted cycloalkanol derivative; and the agricultural and horticultural fungicide which contains the azole-substituted cycloalkanol derivative as an active ingredient and has a fungicidal activity.

The physical properties of the azole-substituted cycloalkanol derivatives and the intermediates for producing the azole-substituted cycloalkanol derivative are shown in Tables 1 to 5.

By the way, these intermediates are the novel compounds except compound No. 1 of Table 4.

Table 1 shows the physical properties of the azole-substituted cycloalkanol derivatives of the following stereoisomers of Types A and B.

TABLE 1

| No. of Compd | Symbol in Formula (I) n | Symbol in Formula (I) A | Type of Stereo-Isomer | Melting Point (°C.) | NMR Spectral Data (CDCl₃,δppm) |
|---|---|---|---|---|---|
| 1 | 1 | N | A | 142–143 | 0.80–2.17 (m,9H); 2.17–3.23 (m,3H); 4.12 (d,1H,J=14Hz); 4.43 (d,1H,J=14Hz); 6.67 (d,2H,J=8Hz); 6.87 (d,2H,J=8Hz); 7.87 (s,1H); 8.03 |

TABLE 1-continued

| No. of Compd | Symbol in Formula (I) n | A | Type of Stereo-Isomer | Melting Point (°C.) | NMR Spectral Data (CDCl$_3$,δppm) |
|---|---|---|---|---|---|
| 2 | 1 | N | Mixture A:B=1:1 | 120–123 | (s,1H); 0.73–1.90 (m,9H); 1.90–3.40 (m,3H); 4.05 (d,J=14Hz); 4.08 (d,J=14Hz); 4.38 (d,J=14Hz); 4.42 (d,J=14Hz); [Total 2H]; 6.93 (d,2H,J=8Hz); 7.13 (d,2H,J=8Hz); 7.80 (s,1H);7.93 (s); 8.00 (s);[Total 1H] |
| 3 | 1 | CH | A | 159–160 | 0.93–1.87 (m,9H); 2.20–3.40 (m,3H); 3.82 (d,1H,J=14Hz); 4.30 (d,1H,J=14Hz); 6.93 (s,2H);7.07 (d,2H,J=9Hz); 7.30 (d,2H,J=9Hz); 7.50 (s,1H) |
| 4 | 2 | N | A | 92–93 | 1.00–3.13 (m,13H); 4.27 (s,2H);7.03 (d,2H,J=9Hz); 7.20 (d,2H,J=9Hz); 7.85 (s,1H); 8.05 (s,1H) |
| 5 | 2 | N | B | 101–103 | 0.92–2.48 (m,12H); 3.27 (d,1H,J=11Hz); 4.30 (s,2H); 7.15 (d,2H,J=9Hz); 7.35 (d,2H,J=9Hz); 8.03 (s,1H);8.23 (s,1H) |

Figure 1:
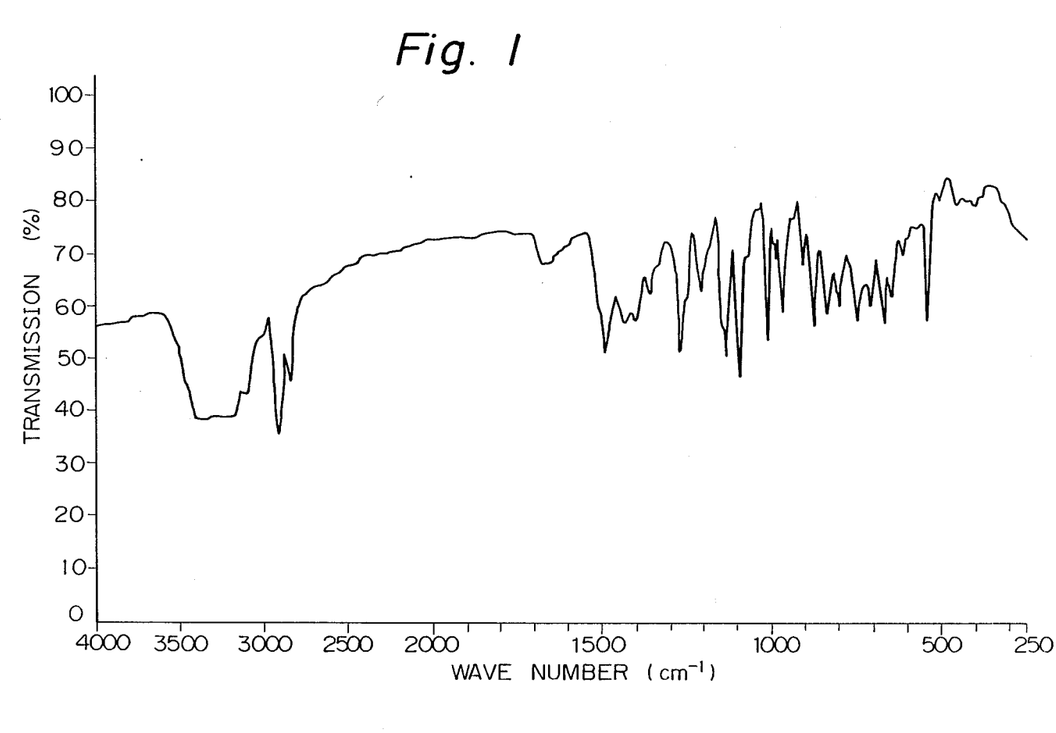
FIGS. 1 to 5 of the attached drawings show the infrared absorption spectra of the azole-substituted cycloalkanol derivatives shown in Table 1. Each of the FIGS. 1 to 5 shows the infrared absorption spectrum of each of the compounds Nos. 1 to 5 shown in Table 1.
Figure 2:
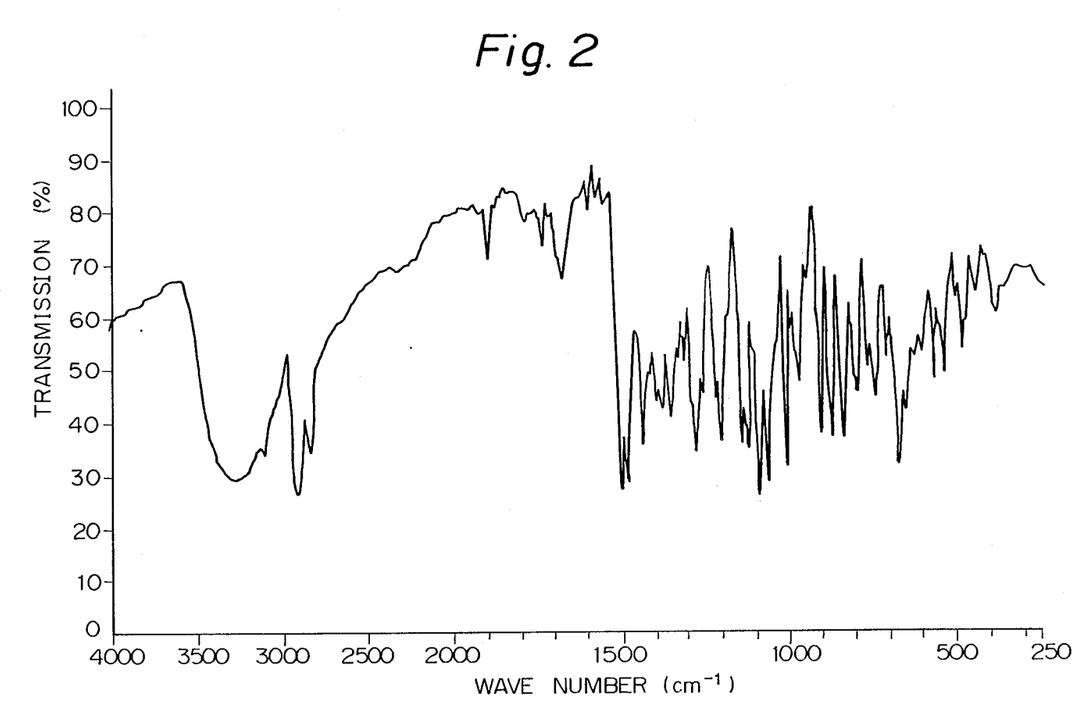
Figure 3:
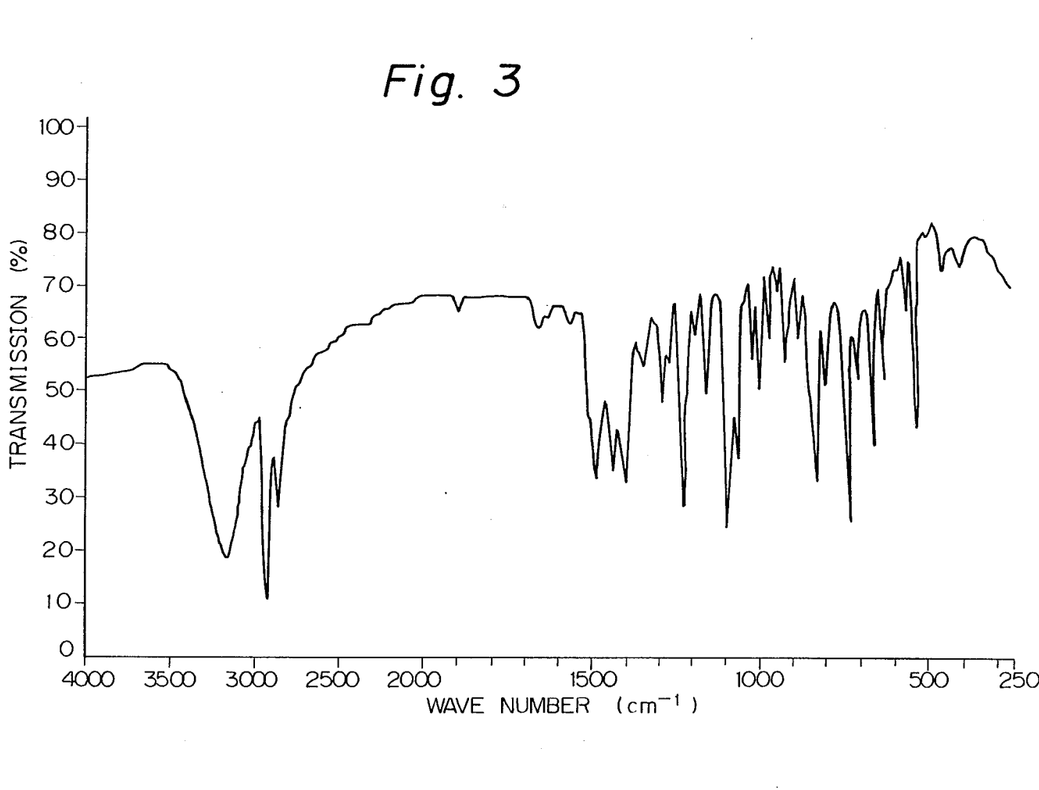
Figure 4:
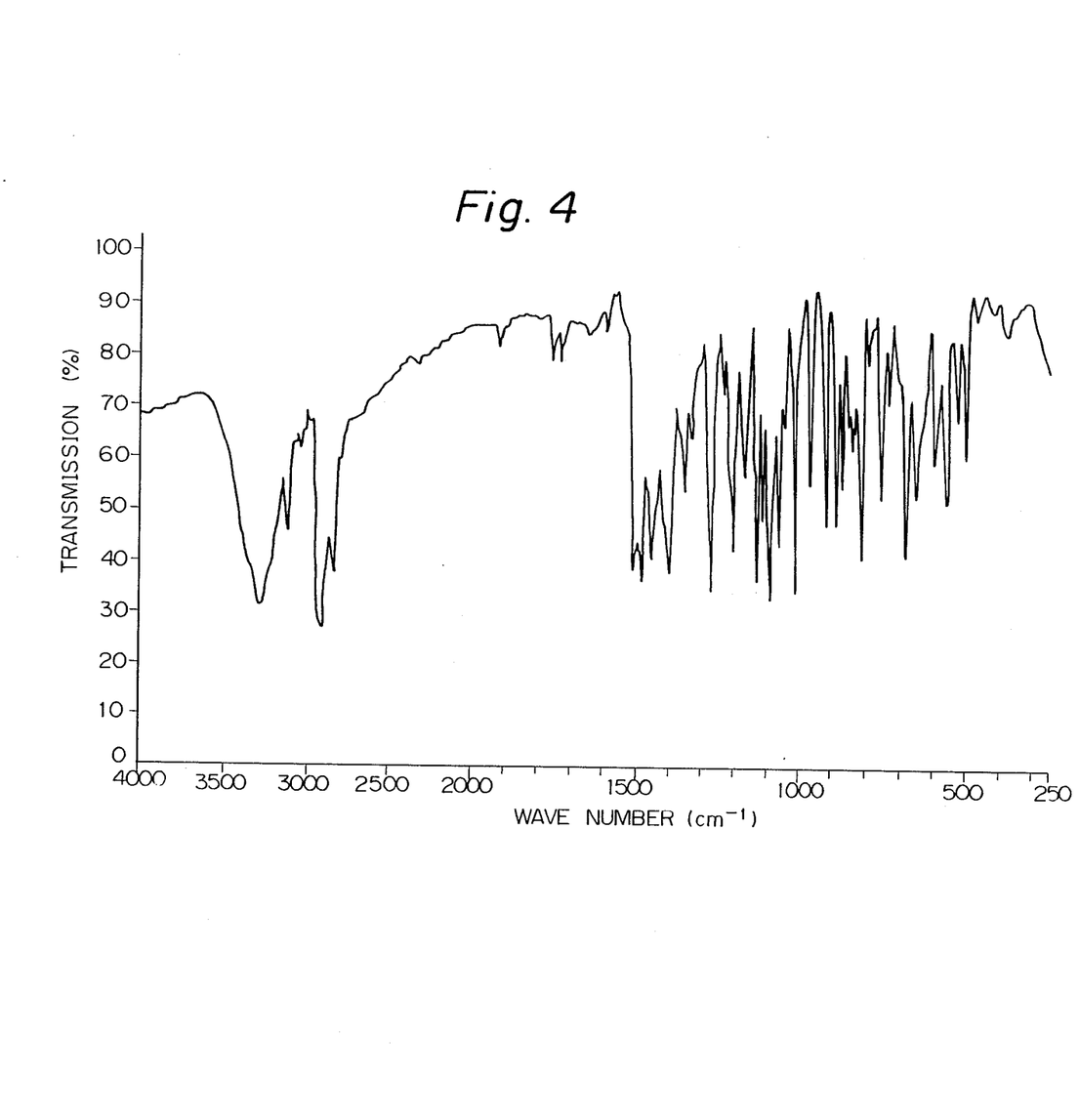
Figure 5:
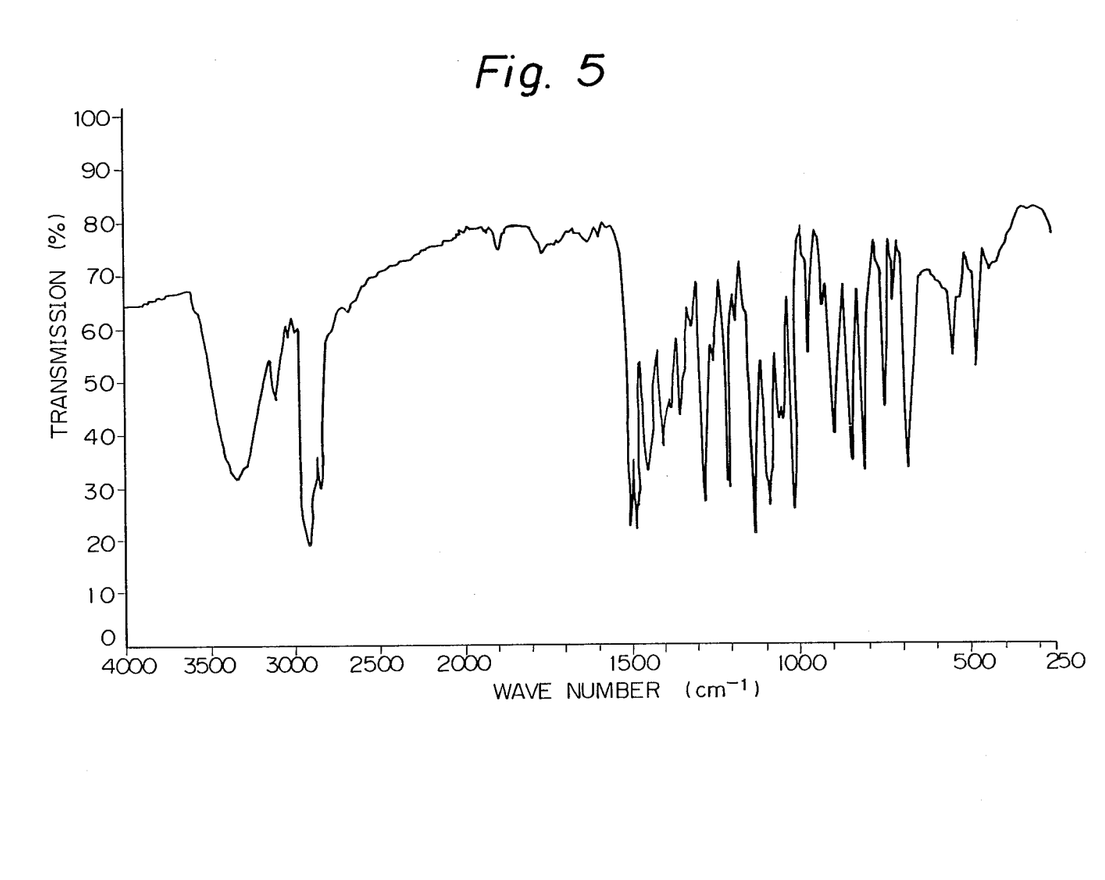

The infrared absorption spectra of the alkanol compounds exemplified in Table 1 are shown in FIGS. 1 to 5 of the attached drawings.

The marks in the above formulae show the stereostructural position of the substituent (or the atom) to the plane, in which the cycloalkane ring exists, as follows: (Hereinafter, in the present invention, these marks are used in the same meanings.)

—group: means the group is in this side of the plane.

group: means the group is in the opposite side of the plane.

Table 2 shows the physical properties of the oxirane derivatives of the following stereoisomers of Types A and B.

(II)

TABLE 2

| No. of Compd | Symbol in Formula (II) n | Type of Stereo-Isomer | Physical Property | NMR Spectral Data (CDCl$_3$,δppm) |
|---|---|---|---|---|
| 1 | 1 | A | Oily | 1.00–2.03 (m,9H); 2.20–3.00 (m,2H); 2.50 (d,1H,J=4Hz); 2.75 (d,1H,J=4Hz); 6.97 (d,2H,J=8Hz); 7.20 (d,2H,J=8Hz); |
| 2 | 1 | Mixture A:B=1:1 | Oily | 1.00–2.07 (m,9H); 2.10–3.00 (m,2H); 2.40 (d,J=5Hz); 2.53 (d,J=5Hz); [Total 1H]; 2.50 (d,J=4Hz); 2.73 (d,J=4Hz); [total 1H]; 6.9 (d,2H,J=8Hz); 7.1 (d,2H,J=8Hz) |
| 3 | 2 | A | Oily | 0.95–2.12 (m,11H); 2.48 (d,d,1H,J=13Hz,10Hz); 2.67 (s,2H); 2.97 (d,d,1H,J=13Hz,4Hz); 7.02 (d,2H,J=8Hz); 7.20 (d,2H,J=8Hz) |
| 4 | 2 | B | Oily | 0.83–2.02 (m,11H); 2.33 (d,d,1H,J=13Hz,8Hz); 2.47 (s,2H); 2.77 (d,d,1H,J=13Hz,6Hz); 7.03 (d,2H,J=8Hz);7.23 (d,2H,J=8Hz) |

Table 3 shows the physical properties of the methylenecycloalkane derivatives of the following formula (III).

TABLE 3

| No. of Compd, | Symbol in Formula (III) n | Physical Property | NMR Spectral Data (CDCl$_3$, δppm) |
|---|---|---|---|
| 1 | 1 | Oily | 0.87–3.13 (m,11H);4.47–4.72 (m,2H);7.00 (d,2H,J=8Hz);7.20 (d,2H,J=8Hz) |
| 2 | 2 | Oily | 0.67–2.70 (m,13H);4.43–4.83 (m,2H);6.98 (d,2H,J=8Hz);7.18 (d,2H,J=8Hz) |

Table 4 shows the physical properties of the cycloalkanone derivatives of the following formula (IV).

TABLE 4

| No. of Compd. | Symbol in Formula (III) n | Physical Property | NMR Spectral Data (CDCl$_3$, δppm) |
|---|---|---|---|
| 1 | 1 | Oily;b.p. 133–135° C. (0.3 mmHg) | 0.93–3.43 (m,11H); 6.97 (d,2H,J=8Hz); 7.17 (d,2H,J=8Hz) |
| 2 | 2 | Oily;b.p. 1.65–170° C. (4.5 mmHg) | 1.00–2.00 (m,8H); 2.28–3.23 (m,5H); 7.03 (d,2H,J=8Hz); 7.23 (d,2H,J=8Hz) |

Table 5 shows the physical properties of the cycloalkanecarboxylic acid ester derivatives of the following formula (V).

(V)

TABLE 5

| No. of Compd. | Symbol in Formula (V) n | R | Physical Property | NMR Spectral Data (CDCl$_3$,δppm) |
|---|---|---|---|---|
| 1 | 1 | CH$_2$CH$_3$ | Solid;m.p. 79–80° C. | 1.17 (t,3H,J=8Hz); 1.37–2.67(m,8H); 2.82 (d,1H,J=14Hz); 3.30 (d,1H, J=14Hz); 4.12 (q,2H,J=18Hz,8Hz); 7.10 (d,2H,J=8Hz); 7.30 (d,2H,J=8Hz) |
| 2 | 2 | CH$_3$ | Oily;b.p. 160–167° C (0.4 mmHg) | 1.27–2.72 (m,10H);2.85 (d,1H,J=14Hz); 3.27 (d,1H,J=14Hz); 3.63 (s,3H); 6.90 (d,2H,J=8Hz); 7.13 (d,2H,J=8Hz) |

The NMR spectra of the compounds shown in Tables 1 to 5 have been determined while taking TMS as the internal standard and they are represented by following symbols:

| s: | singlet, d: doublet, t: triplet, |
|---|---|
| q: | quartet, m: multilet, |
| b: | broad line, J: coupling constant(unit:Hz). |

The process to obtain the azole-substituted cycloalkanol derivative represented by the formula (I) and on the utilization of the azole-substituted cycloalkanol derivatives as an agricultural and horticultural fungicide will be explained next.

The azole-substituted cycloalkanol derivatives according to the present invention are manufactured by the following processes.

By reacting an oxirane derivative represented by the formula (II) with a 1,2,4-triazole or imidazole represented by the following formula (VII):

wherein M represents a hydrogen atom or an alkali metal atom and A represents a nitrogen atom or a CH group, in the presence of a diluent, the objective azole-substituted cycloalkanol derivative represented by the formula (I) is obtained.

The oxirane derivative of the formula (II) used as the starting material of the above reaction can be obtained by the following processes.

Namely, the oxirane derivatives of the formula (II) can be obtained, while referring to the method described, for instance, in Org. Syn. 49, 78 (1969) and J. Am. Chem. Soc. 87, 1353 (1965), by reacting a cycloalkanone represented by the formula (IV) with, for instance, dimethyloxosulfonium methylide or dimethylsulfonium methylide in the presence of a diluent (hereinafter referred to as "the method A").

Further, by an another method (referred to as "the method B"), the oxirane derivative represented by the formula (II) can be obtained, namely, by (i) synthesizing a methylenecycloalkane of the formula (III) from a cycloalkanone of the formula (IV) by the Wittig reaction described in Org. Syn., 40, 66 (1966), and J. Org. Chem. 28, 1128 (1963), and (ii) performing the epoxidation reaction described in Org. Syn. Coll. vol. 4, 552 (1963), and 49, 62 (1969), on the methylenecycloalkane of the formula (III).

The reaction formulae of the methods A and B to synthesize the compound (II) are as follows:

[Method B]

Further, the cycloalkanone derivatives of the formula (IV) can be obtained by (i) benzylating an alkyl 2-oxocycloalkanecarboxylate of the formula (VI) by a method described in Org. Syn. 45, 7 (1965), and J. Org. Chem., 29, 2781 (1964), into a derivative of the formula (V) and (ii) hydrolyzing and decarboxylating the derivative of the formula (V) obtained.

The reaction model of obtaining the above cycloalkanone derivative (IV) is as follow:

In the above formulae (IV) and (V), R represents a lower alkyl group which generally contains from 1 to 6 carbon atoms, preferably 1 to 4 carbon atoms.

As a diluent used in a series of reactions in the process to produce the compounds represented by the formula (I) of the present invention, hydrocarbons such as benzene, toluene, xylene and hexane; alkyl halides such as methylene chloride, chloroform and carbon tetrachloride; alcohols such as methanol and ethanol; ethers such as diethyl ether, diisopropyl ether and tetrahydrofurane; and others such as acetonitrile, acetone, dimethylformamide and dimethylsulfoxide; can be exemplified.

Further, in the process of producing the derivatives according to the present invention, a base or an acid can be used in addition to the above diluent. As the base, carbonates of an alkali metal such as sodium carbonate and potassium carbonate; hydroxides of an alkali metal such as sodium hydroxide and potassium hydroxide; alcoholates of an alkali metal such as sodium methylate, sodium ethylate and potassium tertiary butylate; hydrides of an alkali metal such as sodium hydride and potassium hydride; organometallic compounds of an alkali metal such as n-butyllithium; and others such as triethylamine and pyridine can be exemplified.

As the acid, inorganic acids such as hydrochloric acid, hydrobromic acid, hydroiodic acid and sulfuric acid; and organic acids such as formic acid, acetic acid, butyric acid and p-toluenesulfonic acid can be exemplified.

As the process to produce the compound according to the present invention, for instance, to produce a cycloalkane carboxylic acid ester derivative represented by the formula (V), 4-chlorobenzyl halide is to be reacted with the solution of the compound of the formula (VI) in the above diluent and if necessary, in the presence of the base.

As the reaction temperature, any temperature from solidifying point to boiling point of the above diluent can be applied.

The compound of the formula (IV) can be obtained by hydrolyzing and decarboxylating the cycloalkane carboxylic acid ester derivative of the formula (V) with the above inorganic acid or organic acid. The reaction time in this case is in the range of 2 to 18 hours and the reaction with stirring is better.

To produce the oxirane derivatives of the formula (II) by the method A, a solution obtained by dissolving the cycloalkanone derivative of the formula (IV) in the diluent (dimethylsulfoxide if particularly preferable) is added to dimethyloxosulfonium methylide or dimethylsulfonium methylide which has been prepared by mixing the above base (for example, sodium hydride) and trimethylsulfoxonium iodide or trimethylsulfonium iodide in the equimolar amount, to react each other. Further, the amount of dimethyloxosulfonium methylide or dimethylsulfonium methylide to be reacted is preferably 1.0 to 2.0 equivalent to the cycloalkanone derivative of the formula (IV). The reaction temperature in the range of 25° to 100° C. and the reaction time in the range of 1 to 40 hours are preferable.

To produce the oxirane derivatives of the formula (II) by the method B, (i) a methylcycloalkane derivative of the formula (III) is obtained by adding a cycloalkanone derivative of the formula (IV) to triphenylphosphine methylide (Wittig reagent), which is prepared by mixing the above base (for example, sodium hydride) and methyltriphenylphosphonium halide in the equimolar amount in the diluent (dimethylsulfoxide is particularly preferable); (ii) the methylcycloalkane derivative obtained is dissolved in the diluent; (iii) hydrogen peroxide or an organic peracid, such as peracetic acid, perbenzoic acid or m-chloroperbenzoic acid, is added to the solution and (iv) a reaction between them is performed at the temperature in the range of a room temperature to a boiling point of the diluent.

The oxirane compounds (II), obtained from the cycloalkanone derivative (IV) by the method A or B, have the following stereoisomeric structures concerning the three-dimentional configuration of the oxirane group and the 4-chlorobenzyl group on positions 3 and 4 of the spiro-ring:

(II-A Type)

(II-B Type)

Separation of these stereoisomers, II-A and II-B, from each other can be done, for instance, by chromatography (thin layer chromatography, column chromatography, liquid high performance chromatography, etc.). The features of these stereostructures can be indicated, for instance, by NMR spectra.

As an example of the method to obtain azole-substituted cycloalkanols of the formula (I), 0.5 to 1.0 equivalent of oxiranes of the formula (II) is added to the solution, which is prepared by dissolving azoles of the formula (VII), in the presence of the above base, if necessary, or otherwise, a salt of the azoles of the formula (VII) is added to the solution prepared by dissolving said oxiranes in said diluent.

As a reaction temperature, although any temperature in the range of a solidifying point to a boiling point of the diluent can be applied to the reaction, it is preferable to perform the reaction at the temperature in the range of 0° to 100° C. For the reaction time, 1 to 6 hours reaction with stirring is preferable.

After the reaction is over, the reaction mixture is cooled by pouring into iced water. Then, the mixture is extracted with an organic solvent, such as ethyl acetate, chloroform or benzene and the organic solvent layer is separated, washed with water and dried.

Then, the solvent in the layer is distilled out under a reduced pressure, the residue obtained is purified and the objective compound is obtained. The purification step can be a recrystallization procedure or a silica gel column chromatography.

As the oxirane compounds of the formula (II) have two stereoisomers, (II-A) and (II-B), as described before, cycloalkanol derivatives of the formula (I), which are prepared by reacting said oxirane compound with 1,2,4-triazole or imidazole, must have two stereoisomers, (I-A type) and (I-B type), of the following formulae:

(I-A type)

-continued (I-B type)

The separation of the two isomers can be done, for instance, by a chromatography.

In the next place, explanation will be given on the utility of the azole-substituted cycloalkanol derivative of the formula (I) according to the present invention as the active ingredient of an agricultural and horticultural fungicide.

The azole-substituted cycloalkanol derivatives according to the present invention have the controlling effect on the plant diseases of a broad range, such as follows:

*Pyricularia oryzae* (P.o.), *Cochliobolus miyabeanus* (C.m.), *Xanthomonas oryzae, Rhizoctonia solani* (R.s.), *Helminthosporium sigmoideum* (H.s.) and *Gibberella fujikuroi* (G.f.) all on rice plant; *Podosphaera leucotricha, Venturia inaequalis, Sclerotinia mali, Alternaria mali,* (A.m.) and *Valsa mali* (V.m.) all on apple tree; *Alternaria kikuchiana* (A.k.), *Phyllactinia pyri, Gymnosporangium haraeonum* and *Venturia nashicola* all on pear tree; *Uncinula necator, Phakospora ampelopsidis* and *Glomerella cingulata* (G.c.) all on grape-vine; *Erysiphe graminis f. sp. hordei, Rhynchosporium secalis, Puccinia graminis* and *Puccinia triformis* all on barley; *Puccinia recondita, Septoria tritici, Puccinia triformis* and *Erysiphe graminis f. sp. tritici* all on wheat; *Sphaerotheca fuliginea* and *Colletotrichum lagenarium* (C.l.) all on melon; *Fusarium oxysporum f. niveum* (F.n.) on watermelon; *Fusarium oxysporum f. cucumerinum* (F.c.) on cucumber; *Fusarium oxysporum f. raphani* (F.r.) on radish; *Erysiphe cichoracearum* and *Alternaria solani* all on tomato; *Erysiphe cichoracearum* on egg plant; *Sephaerotheca humuli* on strawberry; *Erysiphe cichoracearum* and *Alternaria longipes* all on tobacco; *Cercospora beticola* (C.b.) on sugar beat; *Alternaria solani* on potato; *Septoria glycinos* and *Cercospora kikuchii* on soybean, *Sclerotinia cinerea* (S.c.) on peach tree, *Botrytis cinerea* (Bo.c.) and *Sclerotinia sclerotiorum* (S.s.) both attacking various crops. Abbreviations in parenthesis above will be used in Table 9.

Furthermore, the azole-substituted cycloalkanol derivatives according to the present invention exhibit not only the preventive control effect but also the curative control effect on several diseases among the above.

In order to apply the azole-substituted cycloalkanol derivatives of the formula (I) as the fungicide described above, said compounds are, by themselves, or after mixing with a carrier (diluent), used favorably in the form of powders, wettable powders, granules, emulsifiable concentrate and liquid.

Moreover, by adding an auxiliary agent such as spreaders, emulsifiers, wetting agents, stickers etc., according to necessity, over the carrier described above, it is possible to make the effect of the compounds more certain.

Incidentally, since the present compounds contain a 1,2,4-triazole ring or an imidazole ring, they can also be used as an inorganic salt, an organic salt or a metal complex salt.

Since an azolylmethyl group and 4-chlorobenzyl group are contained as substituents at the positions 1 and 2 of the cycloalkane ring in the present compound, there are geometric isomers of cis and trans and also optical isomers, however, as the fungicide, all the single isomers and also mixtures thereof in any ratio can be used.

Accordingly, it should be understood that the agricultural and horticultural fungicide according to the present invention includes those which contain any one of single isomers or mixtures thereof as the active ingredient.

The concrete process for producing the azole-substituted cycloalkanol derivatives according to the present invention and the concrete examples of the agricultural and horticultural fungicides having the cycloalkanol derivatives as the active ingredient are shown in the following Examples to explain the effect of the present invention.

In the first place, the synthetic examples of the azole-substituted cycloalkanol derivative represented by the formula (I) and each of the intermediates to produce said azole-substituted cycloalkanol derivative are described as follows.

EXAMPLE 1:

Synthesis of methyl 1-(4-chlorobenzyl)-2-oxocycloheptanecarboxylate (an intermediate compound No. 2 in Table 5):

Into 70 ml of anhydrous dimethylformamide, 3.7 g of sodium hydride (prepared by washing 60% oily sodium hydride with dried hexane) were added while stirring under helium and 25.0 g of methyl 2-oxocyclo-heptanecarboxylate were added to the mixture within 20 minutes. The mixture was stirred for one hour at room temperature. Then, 24.7 g of 4-chlorobenzyl chloride were added to the mixture within 20 minutes and the mixture was further stirred for one hour at 90° C.

After cooling the obtained liquid reaction mixture, it was poured into iced water, extracted with benzene to obtain an organic layer, washed the layer with water and then saline, and dried with anhydrous sodium sulfate. Then the residue was purified by distillation under a reduced pressure to obtain 38.1 g of the compound of the title, having a boiling point of 160° to 167° C./0.4 mmHg.

EXAMPLE 2:

Synthesis of 2-(4-chlorobenzyl)-1-cycloheptanone (the intermediate compound No. 2 in Table 4):

Into 70 ml of 47% hydrobromic acid, 20.0 g of methyl 1-(4-chlorobenzyl)-2-oxocycloheptanecarboxylate (the compound No. 2 in Table 5) were added and the mixture was vigorously stirred for 13 hours at 100° C.

After cooling the obtained liquid reaction mixture, it was poured into iced water, extracted with benzene to obtain an organic layer, washed the layer with an aqueous solution of sodium hydrogen carbonate and then saline and dried with anhydrous sodium sulfate.

Then benzene in the layer was distilled out under a reduced pressure and the residue was purified by distillation under a reduced pressure to obtain 14.2 g of the compound of the title, having a boiling point of 165° to 170° C./4.5 mmHg.

EXAMPLE 3:

Synthesis of 4-(4-chlorobenzyl)-1-oxaspiro[2.6]nonane by the method A (the intermediate compounds Nos. 3 and 4 in Table 2):

Into 15 ml of anhydrous dimethylsulfoxide, 438 mg of sodium hydride (prepared by washing 60% oily sodium hydride with dried hexane) were added while stirring under helium, and then 4.0 g of trimethyloxosulfonium iodide were added to the mixture and the mixture was stirred for 30 minutes at room temperature. Then, 3.3 g of 2-(4-chlorobenzyl)-1-cycloheptanone (the compound No. 2 in Table 4) were added to the mixture and further stirred for 4 hours at 80° C.

After cooling the liquid reaction mixture, it was poured into iced water, and extracted with benzene to obtain an organic layer, washed the layer with saline and dried with anhydrous sodium sulfate.

Then, benzene in the layer was distilled out under a reduced pressure and the residue was purified by silica gel column chromatography and obtained 1.66 g of the compound No. 3 and 0.42 g of the compound No. 4.

EXAMPLE 4:

Synthesis of 2-(4-chlorobenzyl)-1-methylenecycloheptane by the method B (the intermediate compound No. 2 in Table 3):

Into 70 ml of anhydrous dimethylsulfoxide, 2.5 g of sodium hydride (prepared by washing 60% oily sodium hydride with dried benzene) were added under helium, and the mixture was stirred for 5 minutes at 70° C. The liquid reaction mixture was cooled by iced water and then 37.5 g of methyltriphenylphosphonium bromide were added to the cooled mixture and the mixture was stirred for 90 minutes under cooling with water. Then, 10.6 g of 2-(4-chlorobenzyl)-1-cycloheptanone (the compound No. 2 in Table 4) were added to the mixture and the mixture was further stirred for 3 hours at 50° C.

After cooling the reaction liquid, it was poured into iced water and extracted with hexane to obtain an organic layer.

After removing solid triphenylphosphine oxide deposited in the organic layer by filtration, the layer was washed with saline, dried with anhydrous sodium sulfate. Hexane was distilled out from the layer and the residue was purified with silica gel column chromatography to obtain 8.7 g of the compound of the title.

EXAMPLE 5:

Synthesis of 4-(4-chlorobenzyl)-1-oxaspiro[2.6]nonane by the method B (the intermediate compounds Nos. 3 and 4 in Table 2):

Into 100 ml of chloroform, 8.5 g of 2-(4-chlorobenzyl)-1-methylenecycloheptane (the compound No. 2 in Table 3) were dissolved and 12.5 g of m-chloroperbenzoic acid were added to the mixture within 10 minutes and the mixture was stirred for 3.5 hours at room temperature.

Then, 12.0 g of calcium hydroxide were added to the mixture within 10 minutes and the mixture was further stirred for one hour at room temperature.

A deposited solid was removed by filtration and the chloroform layer of the filtrate was concentrated to obtain a colorless oily substance. The oily substance was purified with silica gel column chromatography to obtain 3.3 g of the compound No. 3 and 5.6 g of the compound No. 4.

EXAMPLE 6:

Synthesis of c-2-(4-chlorobenzyl)-1-(1H-1,2,4-triazol-1-ylmethyl)-r-1-cycloheptanol (the compound No. 4 in Table 1):

Into 20 ml of anhydrous dimethylformamide, 200 mg of sodium hydride (prepared by washing 60% oily sodium hydride with dried hexane) were added while stirring under helium and then 574 mg of 1H-1,2,4-triazole were added to the mixture and the mixture was stirred at room temperature until bubbling was stopped.

To the solution obtained, 1.6 g of 4-(4-chlorobenzyl)-1-oxaspiro[2.6]nonane (the compound No. 3 in Table 2) were added and the mixture was stirred for 3 hours at 90° C.

After cooling the liquid reaction mixture, it was poured into iced water, extracted with ethyl acetate to obtain an organic layer, washed the layer with water, dried with anhydrous sodium sulfate and the solvent was distilled out from the layer under a reduced pressure.

The residue obtained was purified with silica gel column chromatography, recrystallized with n-hexane and ethyl acetate and obtained 1.3 g of the compound of the title, having a melting point of 101° to 103° C.

EXAMPLE 7:

Synthesis of c-2-(4-chlorobenzyl)-1-(1H-imidazole-1-ylmethyl)-r-1-cyclohexanol (the compound No. 3 in Table 1):

Into 5 ml of anhydrous dimethylformamide, 120 mg of sodium hydride (prepared by washing 60% oily sodium hydride with dried hexane) were added while stirring under helium and then 340 mg of 1H-imidazole were added to the mixture and the mixture was stirred at room temperature until bubbling was stopped.

Into the solution obtained, 1.0 g of 4-(4-chlorobenzyl)-1-oxaspiro[2.5]octane (the compound No. 1 in Table 2) was added and the mixture was further stirred for 2 hours at 80° C.

After cooling the obtained liquid reaction mixture, it was poured into iced water, extracted with ethyl acetate to obtain an organic layer, washed the layer with water, dried with anhydrous sodium sulfate and the solvent was distilled out from the layer under a reduced pressure. The residue obtained was recrystallized with n-hexane and ethyl acetate to obtain 800 mg of the compound of the title having a melting point of 159° to 160° C.

In the following, several examples will be shown in order to prove the effectiveness of the compounds according to the present invention and the carrier (diluent), the adjuvants, the mixing ratio thereof and the active ingredient can be changed in a broad range.

EXAMPLE 8: Powder:

3 parts by weight of the compound of the present invention (the compound No. 1 in Table 1), 40 parts by weight of clay and 57 parts by weight of talc were pulverized and mixed together and the product is used as a powder.

EXAMPLE 9: Wettable Powder 50 parts by weight of the compound of the present invention (the compound No. 4 in Table 1), 5 parts by weight of lignineselfonic acid, 3 parts by weight of a salt of alkylsulfonic acid and 42 parts by weight of diatomaceous earth were pulverized and mixed together to obtain a wettable powder, which is used after diluting with water.

EXAMPLE 10: Granule 5 parts by weight of the compound of the present invention (the compound No. 3 in Table 1), 43 parts by weight of bentonite, 45 parts by weight of clay and 7 parts by weight of a salt of ligninesulfonic acid were mixed uniformly and after adding water thereto, the mixture was kneaded, processed into granular form by an extruder-type pelletizing machine and the formed pellets were dried into granules.

EXAMPLE 11: Emulsifiable Concentrate 25 parts by weight of the present compound (the compound No. 4 in Table 1), 10 parts by weight of polyoxyethylene alkyl aryl ether, 3 parts by weight of polyoxyethylene sorbitane monolaurate and 62 parts by weight of xylene were mixed uniformly to obtain an emulsifiable concentrate.

EXAMPLE 12: Test for controlling Puccinia recondita on wheat:

On the young seedlings of wheat in the second leaf stage cultured in an unglazed pot of 10 cm in diameter (the variety: NORIN 64, 16 seedlings per pot), the wettable powder prepared by the method described in Example 9 was applied after diluting with water to the predetermined concentration at a rate of 5 ml/pot.

After air drying the applied leaves of the plant, a liquid suspension of the summer spores of *Puccinia recondita* collected from the diseased leaves was sprayed on the seedlings to inoculate the spores. The treated seedlings were kept for 24 hours at a temperature of 20° to 23° C. under a high humidity. Thereafter, the seedlings were left in a green house and after 7 to 10 days of the inoculation, the rate of diseased area of the leaf by *Puccinia recondita* was measured and the protective value of each of the compounds was calculated by the following formula;

$$\text{Protective value}(\%) = (1 - A/B) \times 100$$

wherein A is the rate of disease spot area in the fungicide-applied region and B is the rate of disease spot area in the fungicide-not-applied region (Control).

The results are shown in Table 6 as follows:

TABLE 6

| Test Compound No. in Table 1 | Concentration Applied (ppm) | Protective Value (%) |
| --- | --- | --- |
| 1 | 500 | 85 |
| 2 | 500 | 80 |
| 3 | 500 | 90 |
| 4 | 500 | 100 |
| Control | 0 | 0 |

EXAMPLE 13: Test for controlling Erysiphe graminis f. sp. tritici on wheat:

On the young seedlings of wheat in the second leaf stage cultured in an unglazed pot of 10 cm in diameter (the variety: NORIN 64, 16 seedlings/pot and three pots were used in the fungicide-applied region), the wettable powder prepared by the method described in Example 9 was applied after diluting with water to the predetermined concentration at a rate of 5 ml/pot.

After air drying the applied leaves of the plant, a liquid suspension of the spore of *Erysiphe graminis f. sp. tritici* collected from the diseased leaves was sprayed on the seedlings to inoculate the spores. The treated seedlings were kept for 24 hours at 20° to 24° C. under a high humidity.

Thereafter, the seedlings were left in a green house and after 9 to 11 days of the inoculation, the rate of diseased area of the leaf by *Erysiphe graminis f. sp. tritici* was measured and the protective value of the compound was calculated in the same manner as in Example 12.

The results are shown in Table 7 as follows:

TABLE 7

| Test Compound No. in Table 1 | Concentration Applied (ppm) | Protective Value (%) |
|---|---|---|
| 1 | 500 | 100 |
| 2 | 500 | 100 |
| 3 | 500 | 100 |
| 4 | 500 | 100 |
| 5 | 500 | 95 |
| Control | 0 | 0 |

EXAMPLE 14: Test for controlling Botrytis cinerea on kidney bean plant:

On the leaves of the plant in the first leaf stage cultured in an unglazed pot of 10 cm in diameter (the variety: HON-KINTOKI), the wettable powder prepared as in Example 9 was applied after diluting with water to the predetermined concentration at a rate of 5 ml/pot.

After air drying the applied leaves of the plant, a round piece of agar (4 mm in diameter) containing *Botrytis cinerea* which had been preliminarily cultured for 3 days at 20° C. while using potato sucrose agar medium was directly adhered to the center part of the leaf. The treated plants were kept at 20° to 22° C. under a high humidity. After 3 days of the inoculation, the rate of diseased area of the leaf of the plant by *Botrytis cinerea* was measured and the protective value of each of the compounds was calculated in the same manner as in Example 12.

The results are shown in Table 8 as follows:

TABLE 8

| Test Compound No. in Table 1 | Concentration Applied (ppm) | Protective Value (%) |
|---|---|---|
| 4 | 500 | 100 |
| Control | 0 | 0 |

EXAMPLE 15: Antifungal test against various pathogenic fungi:

This example shows the results of the antifungal test of the azole-substituted cycloalkanol derivatives of the present invention against various pathogenic fungi.

Test Method:

The compound of the present invention was dissolved in dimethylsulfoxide at a predetermined concentration and 0.6 ml of the solution was well mixed with 60 ml of a PSA culture medium at about 60° C. in a conical flask of 100 ml in capacity. The prepared medium was poured into a Petri dish to solidify. On the other hand, the fungus which had been preliminarily cultured on plate culture medium was punched by a corkborer of 4 mm in diameter and the punched piece was inoculated on the plate culture medium containing the present compound. After inoculation, the inoculated plate was cultured for one to three days at the temperature suitable for growing each fungus and the growth of the micelium was determined by the diameter of the colony of the micelium. The result was compared with the growth of the micelium in the control region (not containing the compound).

Namely, the rate of inhibiting the growth of the mycelium is obtained by the following formula:

$$R = [(dc-dt)/dc] \times 100$$

wherein R is the rate of inhibiting the growth of the mycelium (%), dc is the diameter of the colony on the not-treated plate and dt is the diameter of the colony on the plate treated with the compound.

The results were evaluated into 5 stages with the following standards and were shown in Table 9:

The degree of inhibition of growth of the fungi:

5: the rate of inhibiting the growth of the mycelium is higher than 90%.

4: the rate of inhibiting the growth of the mycelium is below 90% and higher than 70%.

3: the rate of inhibiting the growth of the mycelium is below 70% and higher than 40%.

2: the rate of inhibiting the growth of the mycelium is below 40% and higher than 20%.

1: the rate of inhibiting the growth of the mycelium is below 20%.

TABLE 9

| No.*1 | μg/ml*2 | P. o. | C. m. | G. f. | H. s. | R. s. | Bo. c. | S. s. | F. n. | F. c. | F. r. | C. l. | C. b. | S. c. | V. m. | A. k. | A. m. | G. c. |
|---|---|---|---|---|---|---|---|---|---|---|---|---|---|---|---|---|---|---|
| 1 | 100 | 4 | 4 | 4 | 3 | 3 | 4 | 3 | 2 | 3 | 3 | 2 | 4 | 5 | 5 | 3 | 3 | 4 |
| 2 | 100 | 4 | 5 | 4 | 3 | 3 | 5 | 4 | 3 | 3 | 3 | 4 | 4 | 5 | 5 | 3 | 3 | 5 |
| 3 | 100 | 5 | 5 | 5 | 4 | 4 | 3 | 4 | 4 | 5 | 5 | 3 | 3 | 5 | 5 | 4 | 4 | 4 |
| 4 | 100 | 5 | 5 | 5 | 4 | 5 | 5 | 5 | 4 | 4 | 4 | 4 | 5 | 5 | 5 | 4 | 4 | 5 |
| 5 | 100 | 5 | 5 | 4 | 4 | 5 | 4 | 4 | 4 | 4 | 4 | 4 | 4 | 5 | 5 | 4 | 4 | 5 |

*1 Compound Number. Same number as in Table 1 is used.
*2 Concentration of the compound.
*3 Refer to pages 18 and 19 of the specification for the abbreviations of the fungi.

What is claimed is:

1. An azole-substituted cycloalkanol derivative represented by the formula (I):

wherein n is an integer of 1 or 2 and A represents a nitrogen atom.

2. A triazole-substituted cyclohexanol derivative having the three-dimensional configuration represented by the following formula:

3. An equipollent mixture of two triazole-substituted cyclohexanol derivatives having the three-dimensional configurations represented by the following two formulae:

and

4. A triazole-substituted cycloheptanol derivative having the three-dimensional configuration represented by the following formula:

5. A triazole-substituted cycloheptanol derivative having the three-dimensional configuration represented by the following formula:

6. An agricultural and horticultural composition comprising a fungicidally-effective amount of an azole-substituted cycloalkanol derivative represented by the formula (I) as an active ingredient:

wherein n is an integer of 1 or 2 and A represents a nitrogen atom and an agriculturally and horticulturally acceptable carrier.

* * * * *

UNITED STATES PATENT AND TRADEMARK OFFICE
CERTIFICATE OF CORRECTION

PATENT NO. : 4,920,138

DATED : April 24, 1990

INVENTOR(S) : ITO et al

It is certified that error appears in the above-identified patent and that said Letters Patent is hereby corrected as shown below:

Title Page:

The Assignee name is mispelled and address incorrectly identified: "Kureha Kagaku Kogyo Kabushiki Kaishi, Chuo, Japan" should be:

--Kureha Kagaku Kogyo Kabushiki Kaisha, Tokyo, Japan--

Signed and Sealed this

Twenty-sixth Day of November, 1991

Attest:

HARRY F. MANBECK, JR.

*Attesting Officer*     *Commissioner of Patents and Trademarks*